US012622680B2

(12) United States Patent
Karasawa

(10) Patent No.: US 12,622,680 B2
(45) Date of Patent: May 12, 2026

(54) ULTRASOUND DIAGNOSTIC APPARATUS AND CONTROL METHOD FOR ULTRASOUND DIAGNOSTIC APPARATUS

(71) Applicant: FUJIFILM Corporation, Tokyo (JP)

(72) Inventor: Hiroyuki Karasawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 128 days.

(21) Appl. No.: 18/467,244

(22) Filed: Sep. 14, 2023

(65) Prior Publication Data

US 2024/0000437 A1    Jan. 4, 2024

Related U.S. Application Data

(63) Continuation of application No. PCT/JP2022/010211, filed on Mar. 9, 2022.

(30) Foreign Application Priority Data

Mar. 22, 2021    (JP) ................................. 2021-047205

(51) Int. Cl.
*A61B 8/00*        (2006.01)
*H04W 24/08*        (2009.01)
(52) U.S. Cl.
CPC .............. *A61B 8/54* (2013.01); *A61B 8/4472* (2013.01); *H04W 24/08* (2013.01)
(58) Field of Classification Search
CPC ....................................................... A61B 8/54
See application file for complete search history.

(56) References Cited

U.S. PATENT DOCUMENTS

2018/0021025 A1    1/2018   Uno et al.
2018/0263600 A1    9/2018   Bell et al.
2022/0117578 A1    4/2022   Adachi et al.

FOREIGN PATENT DOCUMENTS

JP        H04-141157  A     5/1992
JP        2001-314399 A    11/2001
                  (Continued)

OTHER PUBLICATIONS

International Search Report issued in PCT/JP2022/010211; mailed May 31, 2022.
                  (Continued)

*Primary Examiner* — Joseph M Santos Rodriguez
(74) *Attorney, Agent, or Firm* — Studebaker Brackett PLLC

(57)        ABSTRACT

According to the present invention, in an ultrasound diagnostic apparatus and a control method for an ultrasound diagnostic apparatus, there is provided an ultrasound diagnostic apparatus including an ultrasound probe and an apparatus main body to be connected to the ultrasound probe via wireless communication or wired communication, in which a diagnostic purpose setting section is configured to set a diagnostic purpose input from a user, and a wireless communication determination section is configured to determine whether or not to disable the wireless communication according to a wireless communication status in a case where the diagnostic purpose is a predetermined diagnostic purpose. Then, a wireless communication switching section is configured to set the wireless communication to be disabled in a case where it is determined to disable the wireless communication. With this, it is possible to restrict the use of the wireless communication by the user without awareness in an inappropriate wireless communication environment.

11 Claims, 4 Drawing Sheets

(56) References Cited

FOREIGN PATENT DOCUMENTS

| | | | |
|---|---|---|---|
| JP | 2011-72467 | A | 4/2011 |
| JP | 2018-527054 | A | 9/2018 |
| WO | 2016/129544 | A1 | 8/2016 |
| WO | 2021/005637 | A1 | 1/2021 |

OTHER PUBLICATIONS

Written Opinion of the International Searching Authority issued in PCT/JP2022/010211; mailed May 31, 2022.
"Notice of Reasons for Refusal" Office Action issued in JP 2023-508961; mailed by the Japanese Patent Office on Feb. 17, 2026.

TRANSDUCER ARRAY —11

TRANSMISSION AND RECEPTION CIRCUIT —13

PULSAR —51

AMPLIFICATION SECTION —53

AD CONVERSION SECTION —55

BEAM FORMER —57

ULTRASOUND IMAGE GENERATION UNIT —31

SIGNAL PROCESSING SECTION —21

DSC —23

IMAGE PROCESSING SECTION —25

FIG. 4

ULTRASOUND DIAGNOSTIC APPARATUS AND CONTROL METHOD FOR ULTRASOUND DIAGNOSTIC APPARATUS

CROSS-REFERENCE TO RELATED APPLICATIONS

This application is a Continuation of PCT International Application No. PCT/JP2022/010211 filed on Mar. 9, 2022, which claims priority under 35 U.S.C. § 119(a) to Japanese Patent Application No. 2021-047205 filed on Mar. 22, 2021. The above applications are hereby expressly incorporated by reference, in their entirety, into the present application.

BACKGROUND OF THE INVENTION

1. Field of the Invention

The present invention relates to an ultrasound diagnostic apparatus and a control method for an ultrasound diagnostic apparatus in which an ultrasound probe and an apparatus main body are connected via wireless communication or wired communication.

2. Description of the Related Art

An ultrasound diagnostic apparatus is known in which an ultrasound probe and an apparatus main body are connected via wireless communication or wired communication. As described above, in the ultrasound diagnostic apparatus that performs wireless communication between the ultrasound probe and the apparatus main body, the number of communication retries may increase depending on a congestion status of the wireless communication or the like, resulting in a decrease in frame rate, missing a frame in an ultrasound image, temporary communication stops, or the like, and in a worst case, the connection via the wireless communication may be disconnected.

In response to this, WO2016/129544A and JP2018-527054A disclose an ultrasound diagnostic apparatus in which an ultrasound probe and an apparatus main body are connected via wireless communication, and the wireless communication between the ultrasound probe and the apparatus main body is stopped, pairing is performed, or the like based on a transmission radio wave intensity, a received signal strength indicator, or the like.

SUMMARY OF THE INVENTION

As described above, in a case where the frame rate decreases or the frame of the ultrasound image is missing depending on the congestion status of the wireless communication or the like, it significantly hinders diagnosis and procedures in observing the movement of the heart using the ultrasound diagnostic apparatus or moving a puncture needle while observing a position of the puncture needle. WO2016/129544A and JP2018-527054A disclose that the wireless communication between the ultrasound probe and the apparatus main body is stopped, pairing is performed, or the like based on the transmission radio wave intensity, the received signal strength indicator, or the like, but do not disclose that the use of wireless communication is restricted depending on diagnostic purposes.

An object of the present invention is to provide an ultrasound diagnostic apparatus and a control method for an ultrasound diagnostic apparatus capable of restricting the use of wireless communication by a user without awareness in an inappropriate wireless communication environment.

In order to achieve the above-described object, according to the present invention, there is provided an ultrasound diagnostic apparatus including an ultrasound probe and an apparatus main body to be connected to the ultrasound probe via wireless communication or wired communication, the ultrasound diagnostic apparatus comprising:

a diagnostic purpose setting section configured to set a diagnostic purpose input from a user;

a wireless communication determination section configured to determine whether or not to disable the wireless communication according to a wireless communication status in a case where the diagnostic purpose is a predetermined diagnostic purpose; and a wireless communication switching section configured to set the wireless communication to be disabled in a case where it is determined to disable the wireless communication.

Here, it is preferable that a frame rate memory configured to store a frame rate set in advance, for each diagnostic purpose; and an apparatus control unit configured to operate the ultrasound diagnostic apparatus such that an ultrasound image is displayed at a frame rate corresponding to the diagnostic purpose among the frame rates stored in the frame rate memory are further provided.

In addition, it is preferable that the wireless communication determination section is configured to determine whether or not to disable the wireless communication in a case where the diagnostic purpose requires a frame rate of 20 Hz or higher.

Further, it is preferable that a frame rate memory configured to store a frame rate set in advance, for each diagnostic purpose;

a transmission and reception condition setting section configured to set a transmission and reception condition of an ultrasound wave transmitted and received by the ultrasound probe, according to the diagnostic purpose; and a frame rate comparison section configured to compare a frame rate set according to the diagnostic purpose by the transmission and reception condition setting section with a frame rate corresponding to the diagnostic purpose among the frame rates stored in the frame rate memory are further provided, and that the wireless communication determination section is configured to determine whether or not to disable the wireless communication based on a result of comparison by the frame rate comparison section.

Further, it is preferable that the wireless communication determination section is configured to determine whether or not to disable the wireless communication in a case where the diagnostic purpose is a heart observation mode or a puncture needle observation mode.

Further, it is preferable that a wireless radio wave intensity detection section configured to detect a wireless radio wave intensity of a radio wave signal through the wireless communication is further provided, and that the wireless communication determination section is configured to, in a case where the wireless radio wave intensity is equal to or less than a predetermined threshold value, determine to disable the wireless communication.

Further, it is preferable that the threshold value is −60 dBm.

Further, it is preferable that an error rate detection section configured to detect an error rate of the wireless communication is further provided, and that the wireless communication determination section is configured to, in a case where the error rate is equal to or higher than a predetermined threshold value, determine to disable the wireless communication.

Further, it is preferable that a packet retransmission rate detection section configured to detect a packet retransmission rate of the wireless communication is further provided, and that the wireless communication determination section is configured to, in a case where the packet retransmission rate is equal to or higher than a predetermined threshold value, determine to disable the wireless communication.

Further, it is preferable that a notification section configured to, in a case where it is determined to disable the wireless communication, notify the user of a message for selecting whether or not to use the wireless communication is further provided, and that the wireless communication switching section is configured to switch whether or not to set the wireless communication to be disabled, according to a selection made by the user.

Further, it is preferable that the wireless communication switching section is configured to, in a case where it is determined to disable the wireless communication, forcibly set the wireless communication to be disabled.

In addition, according to the present invention, there is provided a control method for an ultrasound diagnostic apparatus including an ultrasound probe and an apparatus main body to be connected to the ultrasound probe via wireless communication or wired communication, the control method comprising:

a step of setting, via a diagnostic purpose setting section, a diagnostic purpose input from a user;

a step of determining, via a wireless communication determination section, whether or not to disable the wireless communication according to a wireless communication status in a case where the diagnostic purpose is a predetermined diagnostic purpose; and a step of setting, via a wireless communication switching section, the wireless communication to be disabled in a case where it is determined to disable the wireless communication.

In the present invention, it is determined whether or not to disable the wireless communication according to the wireless communication status in a case where the diagnostic purpose is a predetermined diagnostic purpose, and the wireless communication is set to be disabled in a case where it is determined to disable the wireless communication. With this, according to the present invention, in a case where the wireless communication is in an inappropriate environment, the user no longer uses the wireless communication without awareness and can always use the wireless communication in an appropriate wireless communication environment.

BRIEF DESCRIPTION OF THE DRAWINGS

FIG. 4 is a block diagram of one embodiment showing a configuration of a wireless communication control unit.

DESCRIPTION OF THE PREFERRED EMBODIMENTS

Hereinafter, an ultrasound diagnostic apparatus and a control method for an ultrasound diagnostic apparatus of the embodiment of the present invention will be described in detail based on suitable embodiments shown in the accompanying drawings.

Figure 1:
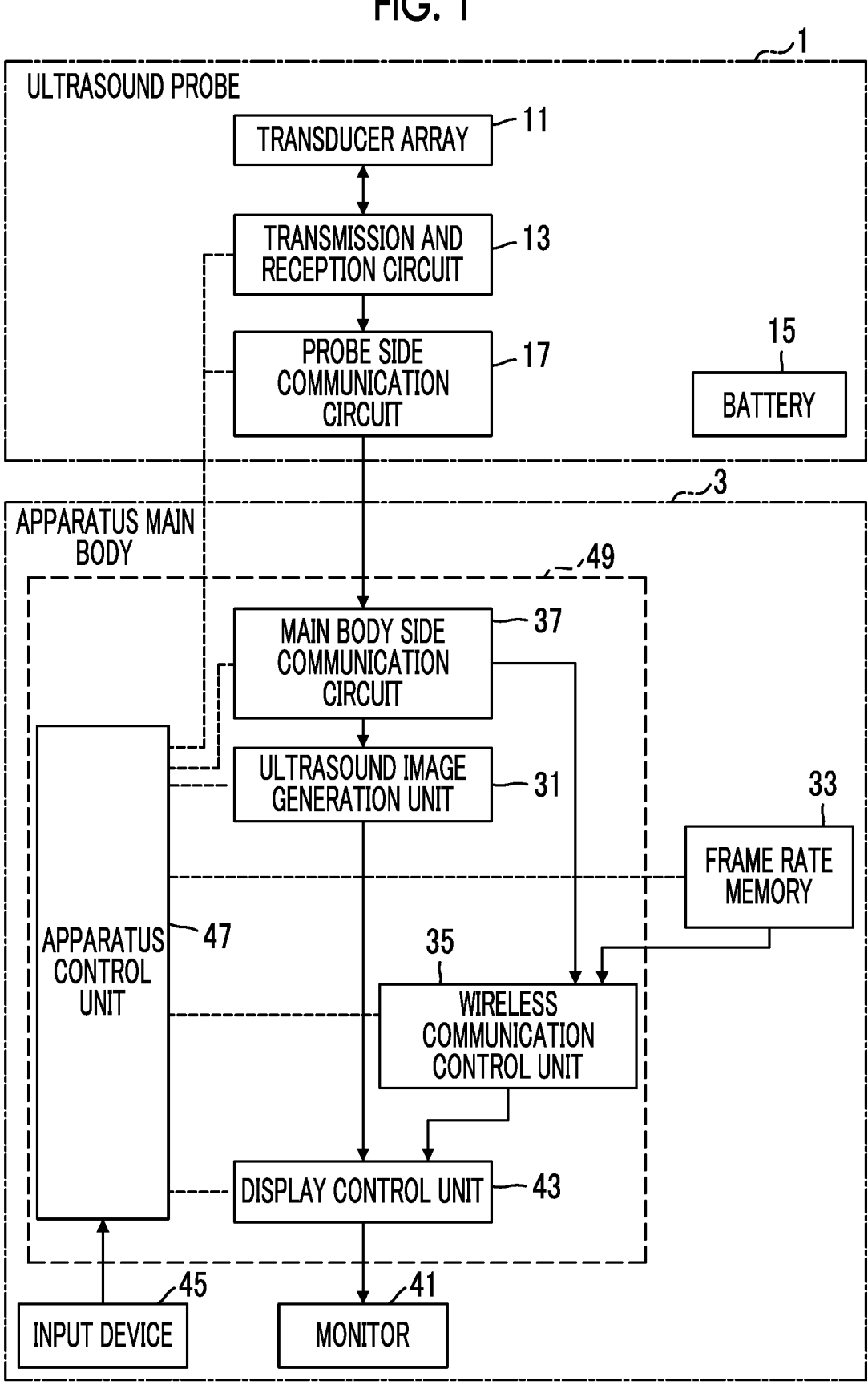
FIG. 1 is a block diagram of one embodiment showing a configuration of an ultrasound diagnostic apparatus of an embodiment of the present invention.

FIG. 1 is a block diagram of one embodiment showing a configuration of the ultrasound diagnostic apparatus of the embodiment of the present invention. The ultrasound diagnostic apparatus shown in FIG. 1 is a handheld ultrasound diagnostic apparatus and comprises an ultrasound probe 1 and an apparatus main body 3 connected to the ultrasound probe 1. The ultrasound diagnostic apparatus of the present embodiment is realized by the ultrasound probe 1, the apparatus main body 3, and an application program for ultrasound diagnosis that operates on the apparatus main body 3.

The ultrasound probe 1 and the apparatus main body 3 are connected via wireless communication using wireless fidelity (Wi-Fi) or the like, or connected via wired communication using a cable, such as a universal serial bus (USB) cable. That is, data is transmitted and received between the ultrasound probe 1 and the apparatus main body 3 via wireless communication or wired communication.

The ultrasound probe 1 scans an examination area of a subject under examination with an ultrasound beam and outputs a sound ray signal corresponding to an ultrasound image of the examination area. As shown in FIG. 1, the ultrasound probe 1 comprises a transducer array 11, a transmission and reception circuit 13, a probe side communication circuit 17, and a battery 15.

The transducer array 11 and the transmission and reception circuit 13 are bidirectionally connected, and the probe side communication circuit 17 is connected to the transmission and reception circuit 13. An apparatus control unit 47 of an apparatus main body 3, which will be described below, is connected to the transmission and reception circuit 13 and the probe side communication circuit 17.

The transducer array 11 includes a plurality of ultrasound transducers arranged one-dimensionally or two-dimensionally. Each of these transducers transmits an ultrasound wave in accordance with a drive signal supplied from the transmission and reception circuit 13 and outputs an analog reception signal by receiving a reflected wave from the subject under examination.

For example, each transducer is composed of an element obtained by forming electrodes at both ends of a piezoelectric body consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

Figures 2, 3:
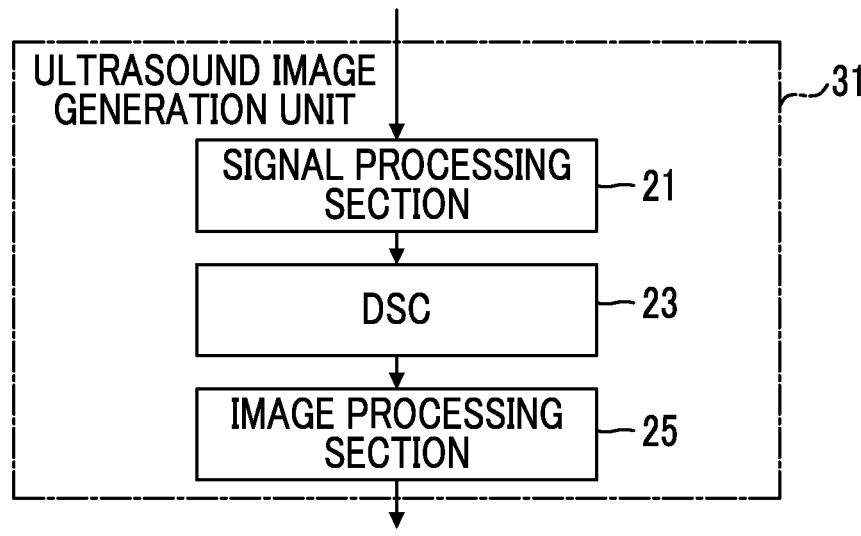
FIG. 2 is a block diagram of one embodiment showing a configuration of a transmission and reception circuit.
FIG. 3 is a block diagram of one embodiment showing a configuration of an ultrasound image generation unit.

Under the control of the apparatus control unit 47, the transmission and reception circuit 13 generates the sound ray signal by transmitting an ultrasound beam from the transducer array 11 and performing reception focus processing on a reception signal output from the transducer array 11, which has received an ultrasound echo. As shown in FIG. 2, the transmission and reception circuit 13 includes a pulsar 51 connected to the transducer array 11, an amplification section 53, an analog-to-digital (AD) conversion section 55, and a beam former 57 that are sequentially connected in series to the transducer array 11.

The pulsar 51 includes, for example, a plurality of pulse generators, and performs transmission focus processing of supplying respective drive signals to the plurality of transducers by adjusting amounts of delay such that ultrasound waves transmitted from the plurality of transducers of the transducer array 11 form an ultrasound beam, based on a transmission delay pattern selected by the apparatus control unit 47. In a case where a pulsed or continuous-wave voltage is applied to the electrodes of the transducer of the transducer array 11 through the transmission focus processing, the piezoelectric body expands and contracts, and a pulsed or continuous-wave ultrasound wave is generated from each of the transducers, whereby the ultrasound beam is formed from a combined wave of these ultrasound waves.

The transmitted ultrasound beam is reflected in, for example, a target such as a site of the subject under examination and propagates toward the transducer array 11 of the ultrasound probe 1. Each of the transducers constituting the transducer array 11 expands and contracts by receiving the ultrasound echo propagating toward the transducer array 11 in this manner, generates a reception signal, which is an electrical signal, and outputs the reception signals to the amplification section 53.

The amplification section 53 amplifies the signal input from each of the transducers constituting the transducer array 11 and transmits the amplified signal to the AD conversion section 55. The AD conversion section 55 converts the analog signal transmitted from the amplification section 53 into digital reception data and outputs the reception data to the beam former 57.

The beam former 57 performs so-called reception focus processing of performing addition by applying a delay to each reception data converted by the AD conversion section 55 in accordance with a sound velocity or a sound velocity distribution set based on a reception delay pattern selected by the apparatus control unit 47. By this reception focus processing, each reception data converted by the AD conversion section 55 is phase-added, and a sound ray signal in which the focus of the ultrasound echo is narrowed down is generated.

The probe side communication circuit 17 transmits and receives data to and from a main body side communication circuit 37 of the apparatus main body 3 via wireless communication or wired communication under the control of the apparatus control unit 47. The probe side communication circuit 17 transmits, for example, the sound ray signal generated by the transmission and reception circuit 13 to the main body side communication circuit 37.

The battery 15 is incorporated into the ultrasound probe 1 and supplies power to each circuit of the ultrasound probe 1.

Next, the apparatus main body 3 generates an ultrasound image including the examination area of the subject under examination based on the sound ray signal generated by the ultrasound probe 1 and displays the ultrasound image. The apparatus main body 3 is, for example, a handheld terminal apparatus, such as a smartphone or a tablet personal computer (PC), and comprises the main body side communication circuit 37, an ultrasound image generation unit 31, a frame rate memory 33, a wireless communication control unit 35, a monitor 41, a display control unit 43, an input device 45, and an apparatus control unit 47, as shown in FIG. 1.

The main body side communication circuit 37 is connected to the probe side communication circuit 17 of the ultrasound probe 1, and the ultrasound image generation unit 31, the display control unit 43, and the monitor 41 are sequentially connected to the main body side communication circuit 37. The wireless communication control unit 35 is connected to the main body side communication circuit 37 and the frame rate memory 33, and the display control unit 43 is connected to the wireless communication control unit 35. The apparatus control unit 47 is connected to the main body side communication circuit 37, the ultrasound image generation unit 31, the frame rate memory 33, the wireless communication control unit 35, and the display control unit 43, and the apparatus control unit 47 is connected to the input device 45.

The main body side communication circuit 37 transmits and receives data to and from the probe side communication circuit 17 of the ultrasound probe 1 via wireless communication or wired communication under the control of the apparatus control unit 47. The main body side communication circuit 37 receives, for example, the sound ray signal transmitted from the probe side communication circuit 17.

Under the control of the apparatus control unit 47, the ultrasound image generation unit 31 generates the ultrasound image (ultrasound image signal) including the examination area of the subject under examination from the reception signal obtained by transmitting and receiving the ultrasound beam to and from the examination area of the subject under examination using the ultrasound probe 1 (more precisely, the transducer array 11), more specifically, from the sound ray signal generated from the reception signal by the transmission and reception circuit 13. As shown in FIG. 3, the ultrasound image generation unit 31 has a configuration in which a signal processing section 21, a DSC 23, and an image processing section 25 are sequentially connected in series.

The signal processing section 21 generates image information data corresponding to the ultrasound image based on the sound ray signal generated by the transmission and reception circuit 13. More specifically, the signal processing section 21 performs signal processing on the sound ray signal generated by the beam former 57 of the transmission and reception circuit 13, for example, corrects the attenuation caused by a propagation distance according to the depth of a position where the ultrasound wave is reflected, and then performs envelope detection processing to generate the image information data representing tomographic image information regarding tissues inside the subject under examination.

The digital scan converter (DSC) 23 raster-converts the image information data generated by the signal processing section 21 into an image signal according to a scanning method of a normal television signal.

The image processing section 25 performs various types of image processing such as brightness correction, gradation correction, sharpness correction, image size correction, refresh rate correction, scanning frequency correction, and color correction according to a display format of the monitor 41 on the image signal input from the DSC 23 to generate the ultrasound image, and outputs the ultrasound image, which has been subjected to the image processing, to the display control unit 43.

The frame rate memory 33 stores a frame rate set in advance, for each diagnostic purpose. That is, the frame rate is uniquely set in the frame rate memory 33 according to the diagnostic purpose.

The frame rate corresponding to each diagnostic purpose is not particularly limited and is appropriately set according to the diagnostic purpose. Conditions for deciding on the frame rate corresponding to the diagnostic purpose include whether or not to use a pulse repetition frequency (PRF), a scan density, a scan width, a spatial compound condition, tissue harmonic imaging (THI), and the like.

For example, in a case of an abdomen observation mode in which abdominal organs, such as the liver, gallbladder, kidneys, pancreas, and spleen, are observed, there is no need to observe the movement, so that the frame rate can be set to 10 Hz, which is relatively low.

On the other hand, in a case of a heart observation mode (including fetal heart observation) in which the size, movement, blood flow, and the like of the heart are observed, there is a need to observe the movement of the heart in real time, so the frame rate can be set to 30 Hz. In a case of a puncture needle observation mode in which a puncture needle is observed in puncturing a puncture site, such as an organ or a blood vessel, there is also a need to move the puncture needle while observing the position of the puncture needle in real time, so that the frame rate can be set to 20 Hz.

That is, in a case of an observation mode in which there is a need to observe movements in real time, such as the heart observation mode and the puncture needle observation mode, a higher frame rate is set than that in a case of an observation mode in which there is no need to observe movements, such as the abdomen observation mode. More specifically, in the case of the observation mode in which there is a need to observe movements in real time, a frame rate of a predetermined threshold value or higher, for example, 20 Hz or higher, is set.

Figure 4:
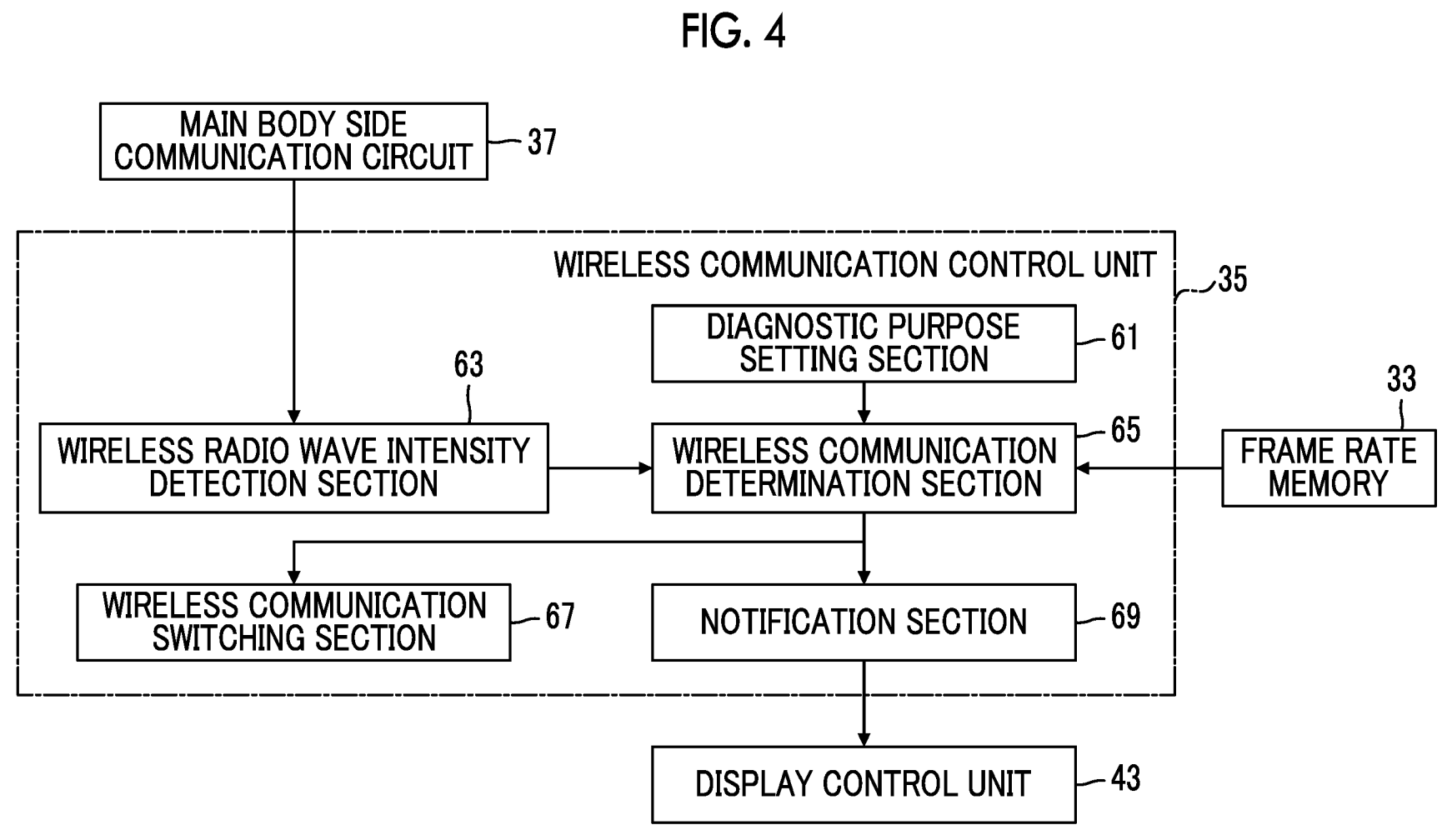

The wireless communication control unit 35 performs various types of processing for controlling the use of wireless communication between the ultrasound probe 1 and the apparatus main body 3 under the control of the apparatus control unit 47. As shown in FIG. 4, the wireless communication control unit 35 includes a diagnostic purpose setting section 61, a wireless radio wave intensity detection section 63, a wireless communication determination section 65, a wireless communication switching section 67, and a notification section 69.

The wireless radio wave intensity detection section 63 is connected to the main body side communication circuit 37. The wireless communication determination section 65 is connected to each of the diagnostic purpose setting section 61, the wireless radio wave intensity detection section 63, and the frame rate memory 33. The wireless communication switching section 67 and the notification section 69 are each connected to the wireless communication determination section 65. The display control unit 43 is connected to the notification section 69.

The diagnostic purpose setting section 61 sets the diagnostic purpose input from the user (examiner) of the ultrasound diagnostic apparatus using the input device 45.

The diagnostic purpose refers to a purpose of performing diagnosis using the ultrasound diagnostic apparatus, in other words, an object to be observed, such as an organ or a puncture needle, using the ultrasound diagnostic apparatus. In the case of the present embodiment, an observation mode corresponding to the object to be observed is used as the diagnostic purpose. The observation mode is not particularly limited, but includes the abdomen observation mode, the heart observation mode, the puncture needle observation mode, and the like described above.

The wireless radio wave intensity detection section 63 detects the wireless radio wave intensity of the radio wave signal through the wireless communication between the ultrasound probe 1 and the apparatus main body 3.

The method of detecting the wireless radio wave intensity is not particularly limited. For example, in the main body side communication circuit 37, the radio wave signal wirelessly received from the probe side communication circuit 17, that is, a received signal strength indicator (RSSI) of the sound ray signal, can be detected.

The wireless communication determination section 65 determines whether or not to disable the wireless communication according to the wireless communication status in a case where the diagnostic purpose set by the diagnostic purpose setting section 61 is the predetermined diagnostic purpose.

The wireless communication status is not particularly limited as long as it can be determined whether or not the wireless communication is in an appropriate environment, but in the case of the present embodiment, the above-described wireless radio wave intensity is used.

As described above, the frame rate is uniquely set according to the diagnostic purpose. Then, under the control of the apparatus control unit 47, the operation of each unit of the ultrasound diagnostic apparatus is controlled such that the ultrasound image is displayed on the monitor 41 at a frame rate corresponding to the diagnostic purpose. However, depending on the congestion status of wireless communication or the like, data for a frame may not be transmitted from the ultrasound probe 1 to the apparatus main body 3 within a time corresponding to the frame rate, resulting in a decrease in frame rate or missing a frame in an ultrasound image.

In this case, it is not a problem for the case of the observation mode in which there is no need to observe movements, such as the abdomen observation mode, but a problem arises in the case of the observation mode in which there is a need to observe movements in real time, such as the heart observation mode and the puncture needle observation mode.

In the case of the heart observation mode, there is a need to observe the movement of the heart in real time. Therefore, the frame rate decreases or the frame of the ultrasound image is missing, which poses a problem that it is very difficult to determine whether the actual movement of the heart has changed or it is due to the problem with the wireless communication. In the case of the puncture needle observation mode, there is a need to move the puncture needle while observing the position of the puncture needle in real time. Therefore, it is very dangerous in a case where the frame rate decreases or the frame of the ultrasound image is missing.

In response to this, the wireless communication determination section 65 determines whether or not to disable the wireless communication in a case where the diagnostic purpose set by the diagnostic purpose setting section 61 is the observation mode in which there is a need to observe movements in real time, in other words, in a case of an observation mode in which a relatively high frame rate is required.

For example, the wireless communication determination section 65 determines whether or not to disable the wireless communication in a case where the diagnostic purpose set by the diagnostic purpose setting section 61 requires a frame rate of a predetermined threshold value or higher, for example, 20 Hz or higher.

Alternatively, the wireless communication determination section 65 determines whether or not to disable the wireless communication in a case where the diagnostic purpose set by the diagnostic purpose setting section 61 is an observation mode in which there is a need to observe movements in real time, such as the heart observation mode, the puncture needle observation mode, or the like.

The wireless communication switching section 67 switches the wireless communication between the ultrasound probe 1 and the apparatus main body 3, in other words, the wireless communication between the probe side communication circuit 17 and the main body side communication circuit 37, to be enabled or to be disabled according to the determination result by the wireless communication determination section 65. That is, the wireless communication switching section 67 sets the wireless communication to be enabled in a case where it is determined to enable the wireless communication, and sets the wireless communication to be disabled in a case where it is determined to disable the wireless communication.

The notification section 69 notifies the user of various messages. For example, the notification section 69 notifies the user of a message indicating that the wireless communication is disabled or notifies the user of a message for selecting whether or not to use the wireless communication, in a case where the wireless communication determination section 65 determines to disable the wireless communication.

The method of the notification is not particularly limited, but for example, the above-described message can be output from the notification section 69 to the display control unit 43 and then this message can be displayed on the monitor 41 by the display control unit 43, or this message can be output from the notification section 69 to a speaker (not shown) and then the message can be output as an audio message to be read aloud by the speaker. Alternatively, both the methods can be performed at the same time.

The display control unit 43 displays various types of information on the monitor 41 under the control of the apparatus control unit 47.

Under the control of the display control unit 43, the monitor (display unit) 41 displays, for example, the ultrasound image generated by the ultrasound image generation unit 31 and the message output from the notification section 69. The monitor 41 is not particularly limited, but examples thereof include a liquid crystal display (LCD) and an organic electro-luminescence (EL) display.

The input device 45 receives various instructions input from the user. The input device 45 is not particularly limited, but includes, for example, various buttons, a touch panel on which the user performs a touch operation to input various instructions, and the like.

The apparatus control unit 47 controls each unit of the ultrasound probe 1 and the apparatus main body 3 based on a program stored in advance and an instruction or the like of the user input through the input device 45.

In the case of the present embodiment, the ultrasound image generation unit 31, the wireless communication control unit 35, the display control unit 43, and the apparatus control unit 47 are configured by a processor 49.

Figure 5:
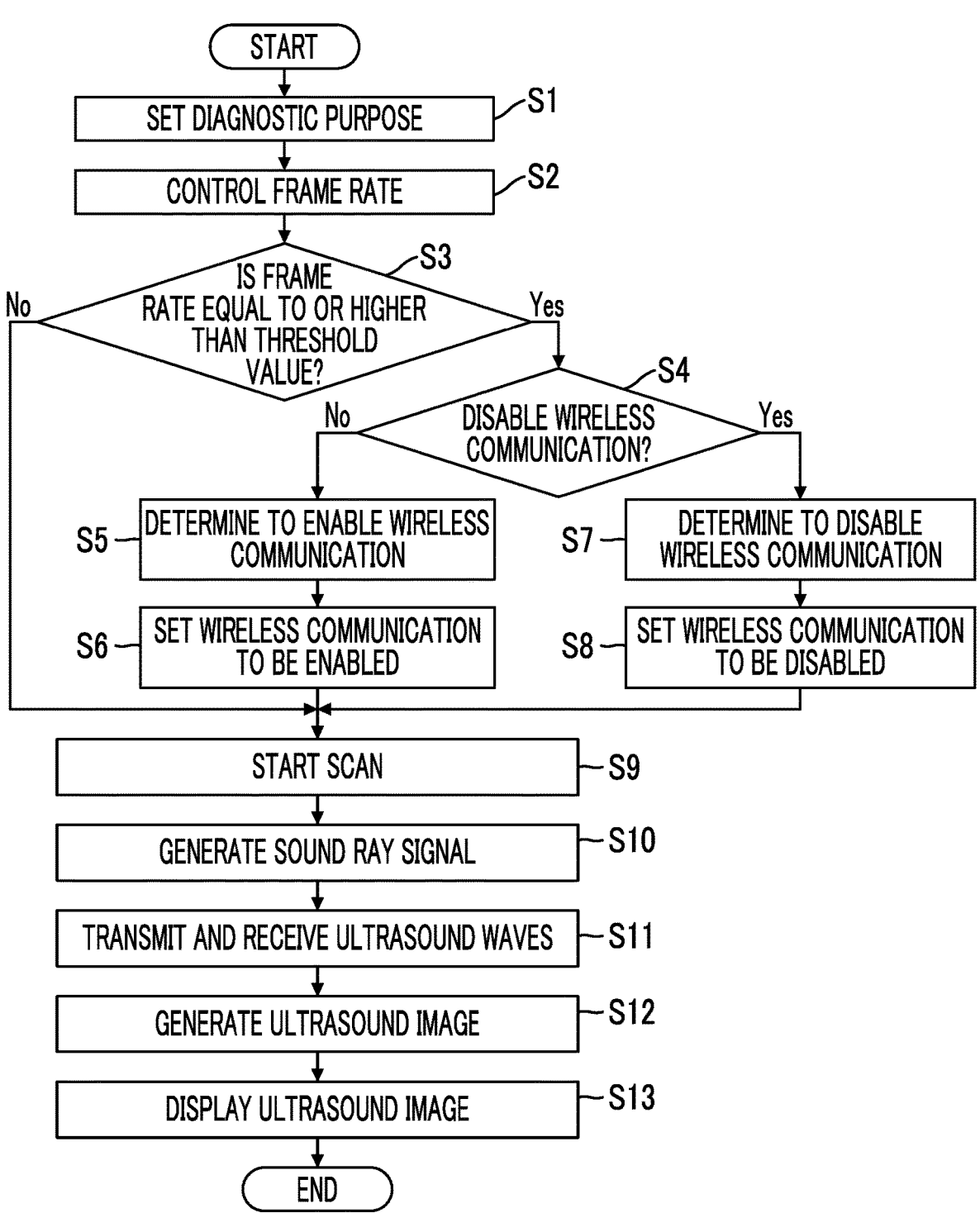
FIG. 5 is a flowchart of one embodiment showing an operation of the ultrasound diagnostic apparatus.

Next, the operation of the ultrasound diagnostic apparatus in a case of generating the ultrasound image will be described with reference to the flowchart of FIG. 5.

In a case of performing the examination, first, the user inputs the diagnostic purpose using the input device 45.

In response to this, under the control of the apparatus control unit 47, the diagnostic purpose input from the user is set by the diagnostic purpose setting section 61 (step S1).

In a case where the diagnostic purpose is set by the diagnostic purpose setting section 61, the frame rate is controlled by the apparatus control unit 47 (step S2). As a result, under the control of the apparatus control unit 47, each unit of the ultrasound diagnostic apparatus operates such that the ultrasound image is displayed on the monitor 41 at a frame rate corresponding to the diagnostic purpose set by the diagnostic purpose setting section 61 among the frame rates stored in the frame rate memory 33.

In addition, in a case where the diagnostic purpose is set by the diagnostic purpose setting section 61, the wireless communication determination section 65 determines whether or not the diagnostic purpose set by the diagnostic purpose setting section 61 requires a frame rate of a predetermined threshold value or higher, for example, 20 Hz or higher, in other words, whether or not the frame rate corresponding to the diagnostic purpose set by the diagnostic purpose setting section 61 is equal to or higher than the predetermined threshold value, for example, 20 Hz (step S3).

As a result, in a case where the diagnostic purpose set by the diagnostic purpose setting section 61 does not require a frame rate of the predetermined threshold value or higher, that is, 20 Hz or higher (No in step S3), the determination by the wireless communication determination section 65 is not performed, and the process proceeds to step S9.

In this case, the user can select whether to connect the ultrasound probe 1 and the apparatus main body 3 via wireless communication or via wired communication.

On the other hand, in a case where the diagnostic purpose set by the diagnostic purpose setting section 61 requires a frame rate of the predetermined threshold value or higher, that is, 20 Hz or higher (Yes in step S3), the wireless communication determination section 65 determines whether or not to disable the wireless communication based on the wireless communication status, that is, based on whether or not the wireless radio wave intensity is equal to or less than a predetermined threshold value, for example, −60 dBm (step S4).

The present invention is not limited to this, and the wireless communication determination section 65 may determine whether or not to disable the wireless communication in a case where a state in which the wireless radio wave intensity is equal to or less than −60 dBm continues for a predetermined time, for example, 10 seconds or more.

As a result, in a case where the wireless radio wave intensity is greater than the predetermined threshold value, that is, −60 dBm (No in step S4), in other words, in a case where the wireless communication is in an appropriate environment, the wireless communication determination section 65 determines to enable the wireless communication (step S5).

In a case where it is determined to enable the wireless communication, the wireless communication switching section 67 sets the wireless communication to be enabled under the control of the apparatus control unit 47 (step S6). After that, the process proceeds to step S9.

In this case as well, the user can select whether to connect the ultrasound probe 1 and the apparatus main body 3 via wireless communication or via wired communication.

On the other hand, the wireless communication determination section 65 determines to disable the wireless communication in a case where the wireless radio wave intensity is equal to or less than the predetermined threshold value, that is, −60 dBm (Yes in step S4), in other words, in a case where the wireless communication is in an inappropriate environment (step S7).

In a case where it is determined to disable the wireless communication, the wireless communication switching section 67 forcibly sets the wireless communication to be disabled under the control of the apparatus control unit 47 (step S8).

In addition, the notification section 69 notifies the user of a message indicating that the wireless communication is disabled. After that, the process proceeds to step S9.

In this case, the user cannot connect the ultrasound probe 1 and the apparatus main body 3 via wireless communication, but can connect them via wired communication.

In a case where it is decided whether the ultrasound probe 1 and the apparatus main body 3 are connected via wireless communication or via wired communication, the user starts scanning using ultrasound waves in a state in which the ultrasound probe 1 is in contact with the examination area of the subject under examination (step S9).

In response to this, under the control of the apparatus control unit 47, the transmission and reception circuit 13 performs the transmission and reception of ultrasound waves in a state in which the ultrasound probe 1 is in contact with the examination area of the subject under examination, thereby generating the sound ray signal (step S10).

That is, the ultrasound beam is transmitted to the examination area of the subject under examination from the plurality of transducers of the transducer array 11 in accordance with the drive signal from the pulsar 51.

The ultrasound echo from the examination area based on the ultrasound beam transmitted from the pulsar 51 is received by each transducer of the transducer array 11, and the reception signal, which is an analog signal, is output from each transducer of the transducer array 11 that has received the ultrasound echo.

The reception signal output from each transducer of the transducer array 11 is amplified by the amplification section 53 and is subjected to AD conversion by the AD conversion section 55, whereby the reception data is acquired.

The sound ray signal is generated by performing the reception focus processing on the reception data through the beam former 57.

Subsequently, the sound ray signal generated by the transmission and reception circuit 13 is transmitted from the probe side communication circuit 17 toward the apparatus main body 3 under the control of the apparatus control unit 47 of the apparatus main body 3 and is received by the main body side communication circuit 37 (step S11).

Subsequently, the ultrasound image generation unit 31 generates an ultrasound image including the examination area of the subject under examination based on the sound ray signal received by the main body side communication circuit 37 under the control of the apparatus control unit 47 (step S12).

That is, the sound ray signal received by the main body side communication circuit 37 is subjected to various types of signal processing by the signal processing section 21, and the image information data representing tomographic image information regarding tissues inside the subject under examination is generated.

The image information data generated by the signal processing section 21 is raster-converted by the DSC 23 and is further subjected to various types of image processing by the image processing section 25, whereby the ultrasound images (video images) are sequentially generated.

Subsequently, the display control unit 43 sequentially displays the ultrasound images generated by the ultrasound image generation unit 31 on the monitor 41 under the control of the apparatus control unit 47 (step S13).

As described above, in the ultrasound diagnostic apparatus of the present embodiment, it is determined whether or not to disable the wireless communication according to the wireless communication status in a case where the diagnostic purpose is a predetermined diagnostic purpose, and the wireless communication is set to be disabled in a case where it is determined to disable the wireless communication. As a result, in a case where the wireless communication is in an inappropriate environment, the user no longer uses the wireless communication without awareness and can always use the wireless communication in an appropriate wireless communication environment.

The wireless communication determination section 65 can use, as the wireless communication status, not only the frame rate stored in the frame rate memory 33 but also a transmission and reception condition (frame rate) of an ultrasound wave actually set according to the diagnostic purpose set by the diagnostic purpose setting section 61.

In this case, for example, a transmission and reception condition setting section and a frame rate comparison section are provided.

The transmission and reception condition setting section sets the transmission and reception condition of the ultrasound wave transmitted and received by the ultrasound probe 1, according to the diagnostic purpose set by the diagnostic purpose setting section 61.

The transmission and reception condition is not particularly limited, but includes a frame rate, a type of probe used for examination (convex, linear, sector, and the like), a transmission frequency of an ultrasound wave, a depth, a gain, and the like. In the case of the present embodiment, the frame rate is used as the transmission and reception condition.

The frame rate comparison section compares the frame rate set according to the diagnostic purpose by the transmission and reception condition setting section with the frame rate corresponding to the diagnostic purpose set by the diagnostic purpose setting section 61 among the frame rates stored in the frame rate memory.

Then, the wireless communication determination section 65 can determine whether or not to disable the wireless communication between the ultrasound probe 1 and the apparatus main body 3 based on the result of comparison by the frame rate comparison section. For example, the wireless communication determination section 65 determines whether or not to disable the wireless communication in a case where the frame rate actually set by the transmission and reception condition setting section is greater than the frame rate corresponding to the diagnostic purpose set by the diagnostic purpose setting section 61.

In addition, the wireless communication determination section 65 may determine whether or not the diagnostic purpose set by the diagnostic purpose setting section 61 is a predetermined specific diagnostic purpose instead of determining whether or not the diagnostic purpose set by the diagnostic purpose setting section 61 requires a frame rate of a predetermined threshold value or higher.

In this case, the wireless communication determination section 65 determines whether or not the diagnostic purpose set by the diagnostic purpose setting section 61 is a predetermined specific diagnostic purpose, for example, the heart observation mode or the puncture needle observation mode.

As a result, in a case where the diagnostic purpose set by the diagnostic purpose setting section 61 is not the specific diagnostic purpose set in advance, that is, the heart observation mode or the puncture needle observation mode, the determination by the wireless communication determination section 65 is not performed.

On the other hand, in a case where the diagnostic purpose set by the diagnostic purpose setting section 61 is the specific diagnostic purpose set in advance, that is, the heart observation mode or the puncture needle observation mode, the wireless communication determination section 65 determines whether or not to disable the wireless communication based on the wireless communication status, that is, based on whether or not the wireless radio wave intensity is equal to or less than the predetermined threshold value, for example, −60 dBm.

In addition, the wireless communication determination section 65 can use at least one of the wireless radio wave intensity, an error rate, or a packet retransmission rate as the wireless communication status, not limited to the wireless radio wave intensity.

In a case where the error rate is used as the wireless communication status, for example, an error rate detection section that detects an error rate of the wireless communication between the ultrasound probe 1 and the apparatus main body 3 is provided.

Then, the wireless communication determination section 65 can determine to disable the wireless communication, in a case where the error rate detected by the error rate detection section is equal to or higher than a predetermined threshold value.

Further, in a case where the packet retransmission rate is used as the wireless communication status, for example, a packet retransmission rate detection section that detects a packet retransmission rate of the wireless communication between the ultrasound probe 1 and the apparatus main body 3 is provided.

Then, the wireless communication determination section 65 can determine to disable wireless communication, in a case where the packet retransmission rate is equal to or higher than a predetermined threshold value.

In addition, in a case where it is determined to disable the wireless communication, the user may select whether or not to use the wireless communication.

In this case, the notification section 69 notifies the user of a message for selecting whether or not to use the wireless communication, and the wireless communication switching section 67 switches whether or not to set the wireless communication to be disabled, according to the selection made by the user. That is, the wireless communication switching section 67 sets the wireless communication to be enabled in a case where the user has selected to use the wireless communication, and sets the wireless communication to be disabled in a case where the user has selected not to use the wireless communication.

In addition, the wireless communication determination section 65 may use a country code from an access point, position information by a global positioning system (GPS), or the like to specify a country in which the ultrasound diagnostic apparatus is used, and determine whether or not to disable the wireless communication between the ultrasound probe 1 and the apparatus main body 3 based on the country in which the ultrasound diagnostic apparatus is used. For example, the wireless communication determination section 65 determines to disable the wireless communication in a case where the country is a country in which the wireless communication between the ultrasound probe 1 and the apparatus main body 3 is not available (including a case where it is unavailable due to legal regulations).

The present invention can be applied to an ultrasound image in a display mode in which the ultrasound image is displayed at a frame rate corresponding to the diagnostic purpose. For example, in addition to an ultrasound image in a brightness (B) mode in which a tomographic image of the examination area of the subject under examination is displayed as a brightness image, an ultrasound image in a color flow (CF) mode in which a direction of blood flow, a flow velocity, and the like are displayed in color in the ultrasound image in the B mode, and the like may be used.

The present invention is not limited to a handheld ultrasound diagnostic apparatus and can also be similarly applied to a stationary ultrasound diagnostic apparatus or a portable ultrasound diagnostic apparatus in which the apparatus main body 3 is realized by a laptop type terminal apparatus as long as wireless communication is performed between the ultrasound probe 1 and the apparatus main body 3. In addition, as shown in FIG. 1, the apparatus main body 3 may comprise the ultrasound image generation unit 31, but the present invention is not limited to this, and all or only the signal processing section 21 of the ultrasound image generation unit 31 may be provided on an ultrasound probe 1 side.

In the apparatus of the embodiment of the present invention, as the hardware configuration of the processing unit that executes various types of processing, such as the transmission and reception circuit 13, the probe side communication circuit 17, the ultrasound image generation unit 31, the wireless communication control unit 35, the main body side communication circuit 37, the display control unit 43, and the apparatus control unit 47, dedicated hardware may be used, or various processors or computers that execute programs may be used. In addition, as the frame rate memory, a semiconductor memory may be used, recording media, such as a flash memory, a secure digital card (SD card), or a universal serial bus memory (USB memory), may be used, or a hard disk drive (HDD), a solid state drive (SSD), an external server, or the like can also be used.

The various processors include a central processing unit (CPU) which is a general-purpose processor that executes software (programs) to function as various processing units, a programmable logic device (PLD) which is a processor whose circuit configuration is changeable after manufacturing, such as a field programmable gate array (FPGA), and a dedicated electric circuit which is a processor that has a dedicated circuit configuration designed to perform specific processing, such as an application specific integrated circuit (ASIC), and the like.

One processing unit may be composed of one of these various processors or may be composed of a combination of two or more processors of the same type or different types, for example, a combination of a plurality of FPGAs, a combination of an FPGA and a CPU, or the like. In addition, a plurality of processing units may be composed of one of the various processors, or two or more of the plurality of processing units may be collectively composed of one processor.

For example, there is an aspect in which one or more CPUs and software are combined to constitute one processor and the processor functions as a plurality of processing units, as represented by a computer such as a client and a server. In addition, there is an aspect in which a processor that realizes functions of an entire system including a plurality of processing units with one integrated circuit (IC) chip is used, as represented by a system on chip (SoC) or the like.

Further, as the hardware configuration of these various processors, more specifically, an electric circuit (circuitry) in which circuit elements, such as semiconductor elements, are combined is used.

In addition, the method of the embodiment of the present invention can be implemented, for example, by a program for causing a computer to execute each of the steps. Further, it is also possible to provide a computer-readable recording medium on which the program is recorded.

Although the present invention has been described in detail above, the present invention is not limited to the above-described embodiment, and various modifications or changes may be made without departing from the gist of the present invention, of course.

EXPLANATION OF REFERENCES

1: ultrasound probe
3: apparatus main body
11: transducer array
13: transmission and reception circuit
15: battery
17: probe side communication circuit
21: signal processing section
23: DSC
25: image processing section
31: ultrasound image generation unit
33: frame rate memory
35: wireless communication control unit
37: main body side communication circuit
41: monitor
43: display control unit
45: input device
47: apparatus control unit
49: processor
51: pulsar
53: amplification section
55: AD conversion section
57: beam former
61: diagnostic purpose setting section
63: wireless radio wave intensity detection section
65: wireless communication determination section
67: wireless communication switching section
69: notification section

What is claimed is:

1. An ultrasound diagnostic apparatus including an ultrasound probe and an apparatus main body to be connected to the ultrasound probe via wireless communication or wired communication, the ultrasound diagnostic apparatus comprising a processor:

the processor being configured to:
set a diagnostic purpose input from a user, the diagnostic purpose referring to an object to be observed using the ultrasound diagnostic apparatus;
operate the ultrasound diagnostic apparatus such that an ultrasound image is displayed at a frame rate corresponding to the diagnostic purpose;
determine whether or not to disable the wireless communication according to a wireless communication status in a case where the diagnostic purpose is a diagnostic purpose which requires a frame rate of a predetermined threshold value or higher; and
set the wireless communication to be disabled in a case where it is determined to disable the wireless communication.

2. The ultrasound diagnostic apparatus according to claim 1, further comprising:
a frame rate memory configured to store a frame rate set in advance, for each diagnostic purpose; and
wherein the processor is configured to operate the ultrasound diagnostic apparatus such that an ultrasound image is displayed at a frame rate corresponding to the diagnostic purpose among the frame rates stored in the frame rate memory.

3. The ultrasound diagnostic apparatus according to claim 1,
wherein the processor is configured to detect a wireless radio wave intensity of a radio wave signal through the wireless communication, and
the processor is configured to, in a case where the wireless radio wave intensity is equal to or less than a predetermined threshold value, determine to disable the wireless communication.

4. The ultrasound diagnostic apparatus according to claim 3,
wherein the threshold value is −60 dBm.

5. The ultrasound diagnostic apparatus according to claim 1,
wherein the processor is configured to, in a case where it is determined to disable the wireless communication, notify the user of a message for selecting whether or not to use the wireless communication, and
the processor is configured to switch whether or not to set the wireless communication to be disabled, according to a selection made by the user.

6. The ultrasound diagnostic apparatus according to claim 1,
wherein the processor is configured to, in a case where it is determined to disable the wireless communication, forcibly set the wireless communication to be disabled.

7. A control method for an ultrasound diagnostic apparatus including an ultrasound probe, an apparatus main body to be connected to the ultrasound probe via wireless communication or wired communication and a processor, the control method comprising:
a step of setting, via the processor, a diagnostic purpose input from a user, the diagnostic purpose referring to an object to be observed using the ultrasound diagnostic apparatus;
a step of operating the ultrasound diagnostic apparatus, via the processor, such that an ultrasound image is displayed at a frame rate corresponding to the diagnostic purpose;
a step of determining, via the processor, whether or not to disable the wireless communication according to a wireless communication status in a case where the diagnostic purpose is a diagnostic purpose which requires a frame rate of a predetermined threshold value or higher; and
a step of setting, via the processor, the wireless communication to be disabled in a case where it is determined to disable the wireless communication.

8. The ultrasound diagnostic apparatus according to claim 2,
wherein the processor is configured to detect a wireless radio wave intensity of a radio wave signal through the wireless communication, and
the processor is configured to, in a case where the wireless radio wave intensity is equal to or less than a predetermined threshold value, determine to disable the wireless communication.

9. The ultrasound diagnostic apparatus according to claim 8,
wherein the threshold value is −60 dBm.

10. The ultrasound diagnostic apparatus according to claim 2
wherein the processor is configured to, in a case where it is determined to disable the wireless communication, notify the user of a message for selecting whether or not to use the wireless communication, and the processor is configured to switch whether or not to set the wireless communication to be disabled, according to a selection made by the user.

11. The ultrasound diagnostic apparatus according to claim 2, wherein the processor is configured to, in a case where it is determined to disable the wireless communication, forcibly set the wireless communication to be disabled.

* * * * *